United States Patent [19]

Ling

[11] 4,131,011
[45] Dec. 26, 1978

[54] METHOD AND DEVICE FOR DETERMINING THE END POINT FOR DRYING

[75] Inventor: Wilfred C. Ling, Lake Bluff, Ill.

[73] Assignee: Abbott Laboratories, North Chicago, Ill.

[21] Appl. No.: 772,719

[22] Filed: Feb. 28, 1977

[51] Int. Cl.² ............................................. G01N 19/10
[52] U.S. Cl. ..................................... 73/29; 73/422 R
[58] Field of Search ............... 73/422 R, 212, 29, 202; 237/59; 236/91 F

[56] References Cited

U.S. PATENT DOCUMENTS

| | | | |
|---|---|---|---|
| 2,256,797 | 9/1941 | Walker | 236/91 F |
| 2,452,224 | 10/1948 | Collett | 73/421.5 R |
| 2,475,857 | 7/1949 | Reinert | 73/421.5 R |
| 2,592,464 | 4/1952 | Plank | 73/422 R |
| 3,000,213 | 9/1961 | Eves et al. | 73/204 |
| 3,425,277 | 2/1969 | Adams | 73/202 |
| 3,443,434 | 5/1969 | Baker | 73/202 |
| 3,803,921 | 4/1974 | Dieterich | 73/422 R |

FOREIGN PATENT DOCUMENTS 629635  9/1949  United Kingdom ............... 237/59

*Primary Examiner*—Anthony V. Ciarlante
*Attorney, Agent, or Firm*—Robert L. Niblack; Neil E. Hamilton

[57] ABSTRACT

A method and device for determining the end point for drying in a stream of flowing fluid which method utilizes a reduction in pressure to effect a bypass of fluid flow through a humidity sensor with return of the sample to the main fluid stream. The method is accomplished by placing a first conduit member with the orifice in a nonconfronting manner with respect to the flow and a second conduit member also in the main channel and spaced from the first conduit. A pressure differential is effected between the orifices so as to effect flow through the first orifice to the sensing device and out through the second orifice. In a preferred manner, a pressure differential is effected by utilizing a larger orifice for the second conduit and positioning both orifices opposite the stream flow. A preferred apparatus for effecting the method utilizes a tubular or pipe member for the first conduit which has a curved portion to present an orifice opposite the flow of fluid. A second conduit similar in shape to the first conduit but larger in diameter, is also curved and positioned with an opening facing downstream of the fluid flow and spaced from the first orifice. The opposing ends of the tubular members are connected to a sensing device such as a humidity sensor which preferably is connected to a signal processor which can be utilized to operate a switch or other control equipment such as regulating a drying oven.

7 Claims, 4 Drawing Figures

METHOD AND DEVICE FOR DETERMINING THE END POINT FOR DRYING

BACKGROUND OF THE INVENTION

This invention relates to a method and apparatus for diverting and sensing a sample portion from a main channel stream of flowing fluid. More particularly, it relates to a method and apparatus for withdrawing a sample portion from a conduit stream of air having an undetermined moisture content which sampling is effected by means of a reduction of pressure to effect flow from the stream to a humidity sensor and return of the sample to the stream. The reduction of pressure to effect the sample flow is effected in a manner such that large particles of moisture or dirt are not drawn into the sensing device.

Sampling devices of the type concerned with in this invention are described in U.S. Pat. Nos. 2,452,224 and 2,475,857. Both of these prior art sampling devices utilize intake tubes or pipes with the orifices facing upstream of the flow of fluid to be sampled. In U.S. Pat. No. 2,452,224, two conduits or tubes are utilized with at least one of their orifices facing fluid flow. These types of arrangements can pose problems in that large particles of moisture and dirt can enter into the sampling system and cause inaccurate readings. If filters are employed, adjustement for undue and undesirable pressure drops across the sampling system must be effected.

It is an advantage of the present invention to provide a noval process and apparatus for diverting and sensing a sample portion from a mainstream of flowing fluid. Other advantages are a method and apparatus for determining the end point for drying wherein the main channel stream is the exhaust air from a drying oven; a diverting and sensing method and apparatus which is particularly suitable for being utilized with a humidity sensor; a method and apparatus for sensing moisture in an air stream which avoids contact or large particles of moisture and dirt with the sensing device; an air sampling device which is simple in its construction, involving a minimum number of parts and readily adaptable to an air flow pipe or conduit.

SUMMARY OF THE INVENTION

The foregoing advantages are accomplished and the shortcomings of the prior art are overcome by the present process and apparatus wherein a first conduit member is placed in a main channel stream of flowing fluid with the orifice of the first conduit member positioned in a nonconfronting manner with respect to the fluid flow. A second conduit member with an orifice is also placed in the channel and spaced from the first conduit member. A pressure differential is effected between the orifices with the pressure at the second orifice being less than that of the first orifice to thereby effect the flow of a portion of the stream into and through the first conduit and out the second conduit while sensing a portion of the stream as it passes through the conduits. In a preferred manner, the orifice of the first conduit is positioned in a direction opposite to the flow of fluid in the mainstream and in a like manner, the orifice of the second conduit. The preferred apparatus for accomplishing the previously described method is a first conduit member with a curved section so as to present a first orifice opposite the fluid stream direction and with a given diameter. The preferred apparatus has a second conduit with a larger diameter tubing and with the orifice of the tubing also positioned in a direction opposite the flow of fluid. The apparatus and method of this invention is preferably utilized with a fluid stream composed of air and moisture and the preferred sensing means is a humidity sensor which can be operatively connected to a signal processor to perform various functions such as closing down a drying operation.

BRIEF DESCRIPTION OF THE DRAWINGS

A better understanding of the present process and the apparatus for accomplishing it will be afforded by reference to the drawing wherein.

DESCRIPTION OF THE PREFERRED EMBODIMENT

The method for diverting and sensing a sample portion from a main fluid stream involves the placement of a first conduit member with an orifice end in fluid-tight communication with a channel for a stream of moisturized air and a second conduit member also with an end orifice in communication with the channel but spaced from the first orifice and downstream thereof. A pressure differential is created between the two orifices with the pressure at the second being less than the first so that a sample portion is caused to flow in through the first orifice and a portion of the stream is then sensed by a sensing device as it passes through the conduits and out through the second orifice. In order to prevent large particles of moisture or dirt from entering through the system, the orifices are preferably positioned so that their openings face in an opposing direction to the fluid flow, or are parallel thereto. In any event, they are positioned in a nonconfronting manner with respect to the air flow. The preferred sensing device is a humidity sensor which in turn can be connected to a signal processor such as a humidity recorder or a humidity indicator with a microcomputer. Such a signal processor could then compute the rate of change of humidity with time and the instrument could generate a signal output either when the computed parameter changes sign or when the humidity decreases to a determined level. The electrical output could then be used to signal an alarm or operate a switch or control a dryer. For example, the sensing device can be used to detect dryness when a water washed process pipe or hose is subjected to compressed air drying. In pharmaceutical production, dryness is important because of possible microbial growth in a wet pipe. Also, dryness is required if the pipe is to be used next for an oil based product. Knowing the exact time of dryness eliminates the hazard of insufficient drying or of overdrying with waste of time and consumption of expensive compressed air. When utilizing the device to monitor a drying oven, the unit would be employed to sample both the inlet and outlet air. In this case the differential humidity can be obtained from the two sensors and the rate of change of differential humidity with time can be computed with a computing element of the instrument. A computed output can be used to trigger an alarm signaling the end of drying. The method should be useful where the falling rate period is either short or nonexistent.

Figure 4:
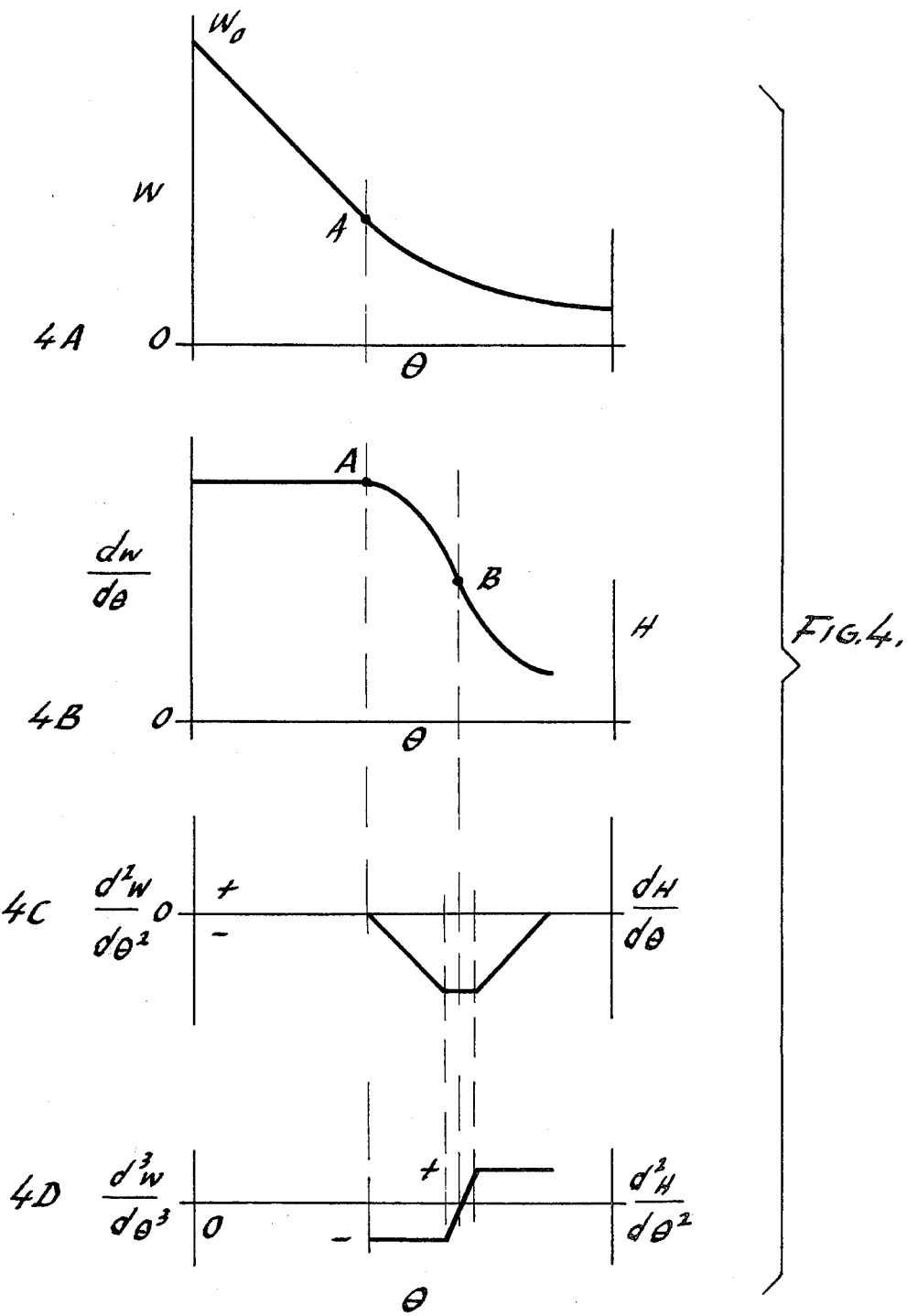
FIG. 4 illustrates four charts, 4A, 4B, 4C and 4D showing certain data utilized in conjunction with the method and apparatus of this invention.

Referring to FIG. 4 and charts 4A, 4B, 4C and 4D, the plots shown in these charts will indicate how the data gathered by the humidity sensor can be utilized during a drying operation. FIG. 4A shows a plot of moisture content, W (weight, i.e. water, solvent, etc.) versus time, $\theta$ during drying of solids where mainly surface moisture is removed. The rate of moisture loss from the beginning to point A is constant. As drying proceeds beyond point A, the rate is slowed down due to the gradual loss of wetted surface.

FIG. 4B shows the plot of drying rate $dW/d\theta$ versus time. It shows the transition from a constant rate to a falling rate period beginning with point A as described before. In a drying oven where inlet and outlet air flow is constant (but not necessarily equal) the humidity of the outlet air approximates that shown in FIG. 4B. In other words, the humidity is a function of drying rate during any point in time of the drying process. Point B is the beginning of the tail end of drying for surface moisture. It can be a useful point of control.

FIG. 4C shows the change of humidity with time. It is comparable to the second derivative of W with time. It shows how the negative slope of H (humidity) versus $\theta$ (time) gets more negative until point B. After point B, the negative slope becomes increasingly less negative. In terms of the second derivative of humidity, $d^2H/d\theta^2$, this transition is indicated by a change from negative to positive values as shown in FIG. 4D. The time at which a change of sign occurs could be utilized as an end point of drying.

Figure 1:
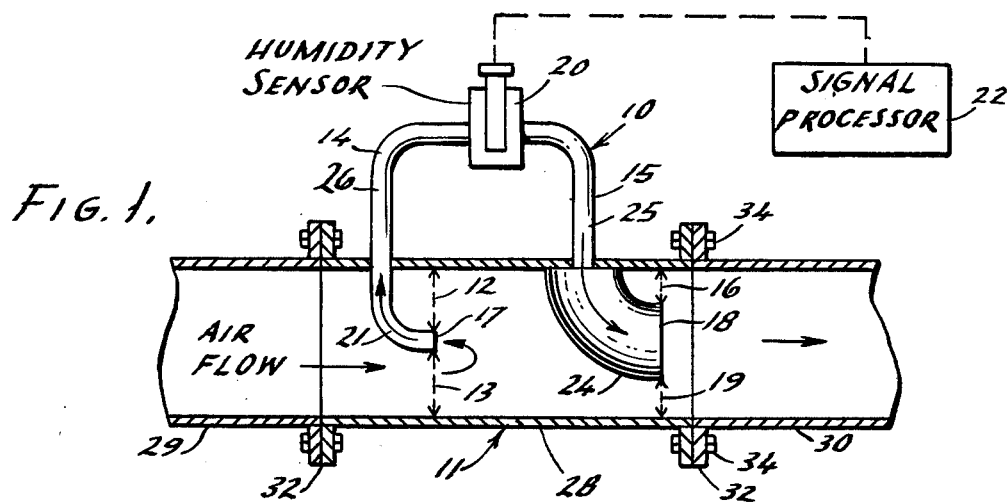
FIG. 1 is a view in side elevation showing one embodiment of an apparatus for sensing a sample portion of fluid from a pipe which is shown in section.
Figure 2:
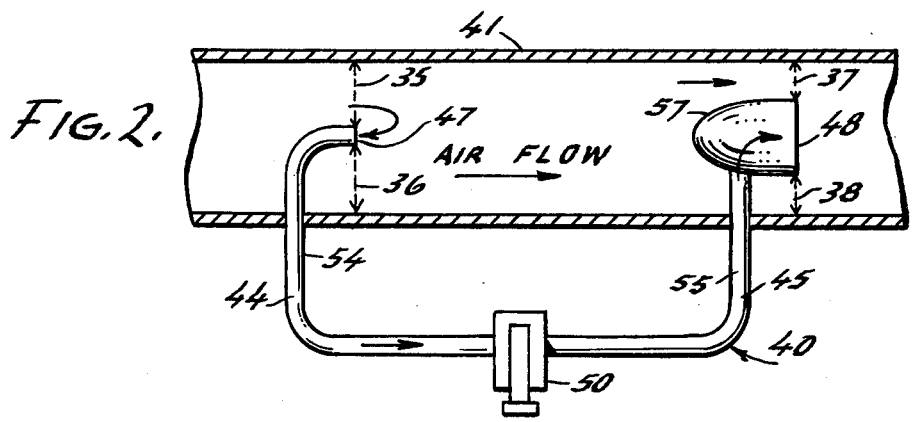
FIG. 2 is a view similar to FIG. 1 showing an alternative embodiment of the apparatus of this invention.
Figure 3:
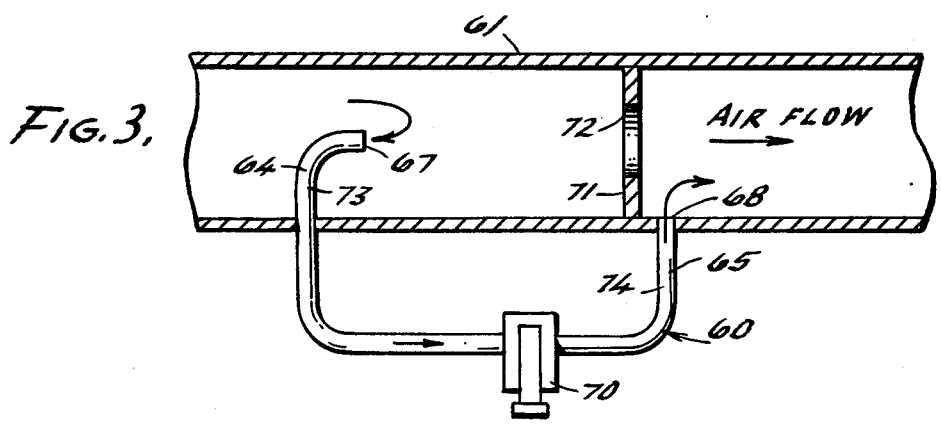
FIG. 3 is a view similar to FIG. 1 showing still another embodiment of the device for diverting and sensing a fluid sample.

The apparatus which can be advantageously employed for the previously referred-to method is shown in FIGS. 1, 2 and 3. A preferred apparatus is that described in FIG. 1 wherein the sensing device 10 is shown operatively connected to a channel member 11 representing a pipe with air flow in the direction of the arrows shown in solid lines. A first conduit 14 has a curved right angle or elbow portion with an orifice 17 positioned in the pipe such that it is opposite the air flow therein. Conduit 14 communicates with a humidity sensing means 20 which in this instance is a Model 880-B2 Thermoelectric Dew Point Hygrometer available from Cambridge Systems, Inc. of Newton, Mass. Preferably, a signal processor 22 is operatively connected to the humidity sensor 20 for the purposes as previously described. A second conduit 15 extends from the opposite side of the humidity sensor 20 and has two tubular sections 24 and 25 with elbow section 24 being located in channel member 11 and in the manner of first conduit 14 has the orifice 18 extending opposite the fluid flow. It will be seen that both tubular sections 26 and 25 are in fluid-tight engagement with pipe section 28 which is interconnected with pipe sections 29 and 30 by means of the usual flanges 32 and bolts 34.

It will be noted in conjunction with FIG. 1, that tubular section 24 is of a much larger diameter than tubular section 26 forming orifice 17. In this particular embodiment, orifice 18 will have an inside diameter of 1 inch and an outside diameter of 1 15/16 inches, while orifice 17 and conduit 14 will have an inside diameter of ¼ inch and an outside diameter of ⅜ inch. The inside diameter of channel member 11 is 2 inches and orifices 17 and 18 will be spaced 4½ inches apart. Conduits 14 and 15 are of the same inside and outside diameter and with section 24 extend approximately four feet. Flow through first and second conduits 14 and 15 and consequently through the humidity sensor 20 is induced by virtue of the differential pressure between the annular sections indicated by the arrows 12, 13, 16 and 19 shown in broken lines. This differential pressure is caused by the restricted cross section area designated by the arrows 16 and 19. In all cases the area ($A_2$) represented by the arrows 16 and 19 must be less than the area ($A_1$) as indicated by the arrows 12 and 13. The exact ratio of $A_2/A_1$ required for a given induced flow depends upon the diameter and flow rate in the main duct 28. For a given duct, the lower the flow rate the smaller must be the ratio $A_2/A_1$ in order to induce adequate flow through the sample tubes 14 and 15. For example, with 2000 cfm air flowing in a 12-inch duct, $A_2/A_1$ must be no more than about 0.9 to induce a sampling air flow of 2,000 cc/min. However, if the flow rate is 1000 cfm in the main duct 28, the $A_2/A_1$ ratio must be reduced to about 0.76 in order to get the same flow of sampling air. These same relationships although not specifically discussed apply in the embodiment shown in FIG. 2 as well as in FIG. 3.

Concerning the FIG. 2 embodiment generally indicated as 40, a first conduit 44 is in fluid-tight engagement with a channel member 41 and is provided by a tubular section 54 having a first orifice 47. A second orifice 48 is provided by means of a dome member 57 interconnected to a tubular section 55 forming a second conduit 45 with conduits 44 and 45 interconnected to a sensing means 50. In this particular embodiment, conduits 44 and 45 are of the same dimensions as conduits 14 and 15 with the vertical leg sections of conduits 44 and 45 spaced from each other approximately 4⅝ inches. Orifice 47 will have an outside diameter of ⅜ inch and an inside diameter of ¼ inch while hollow dome member 57 has an outside diameter of 1 5/16 inches and an inside diameter of 1 inch at the orifice 48. The diameter of duct 41, as is true of duct 11, is 2 inches. The cross section of that annular area represented by arrows 37 and 38 shown in broken lines is about 59% of that of the annular cross sectional area shown by arrows 35 and 36 also represented in broken lines. Compressed air with flow rates of 25.5 to 40.8 standard cubic feet per minute induces a flow in the sampling tube 54 from 430 to 1900 cm³/min.

In FIG. 3 another embodiment is shown which differs from the previous two embodiments in FIGS. 1 and 2 in that the differential pressure at the second orifice indicated by the numeral 68 is not produced by a larger pipe or dome member. Instead it is afforded by means of a restricted passage formed by an annular plate 71 providing an orifice 72 with the second orifice spaced downstream thereof and adjacent thereto as well as parallel to stream flow. In this particular embodiment, the first conduit 64 and the orifice 67 formed therefrom as provided by tubular section 73 will be of the same dimensions as previously indicated for first conduit 44 and orifice 47. The sensing device 60 of this embodiment will also have the sensing means 70 interconnected to the two conduits 64 and 65. Sensing device 60 is utilized in conjunction with channel member or duct 61 having a diameter of 2 inches with orifice 67 having a diameter of ⅜ inch and orifice 72 having an inside diameter of 1½ inches. Orifice 67 will be spaced from plate 71 approximately 6 inches.

Operation

A better understanding of the advantages of sensing devices 10, 40 and 60 will be had by a description of their operation. As the operation of all three embodiments are substantially the same, only the operation in conjunction with FIG. 1 will be described.

Referring to FIG. 1, pipe section 30 will represent a 12 inch exhaust air duct of a drying oven with the air flow at a rate of 1000 cfm. As the air will flow around tubular section 24 and due to the restricted annular area indicated by the arrows 16 and 19, a reduced pressure will be effected in tubular section 24 and consequently in first and second conduits 14 and 15 to thereby draw an air sample with water vapor into orifice 17, sampling tube 26 and consequently to humidity sensing means 20. As previously described, if the annular area represented by arrows 16 and 19 is no more than about 0.76 of the annular area represented by arrows 12 and 13, a sampling air flow of 2000 cc/min. will be effected in the first and second conduits 14 and 15.

By providing a conduit sampling system wherein the orifices are in a nonconfronting position with respect to the air flow, it will be seen that any large particles of moisture or dirt will not be forced into the sampling tubes and consequently adversely affect the humidity sensor. In the embodiment shown in FIG. 3, the second orifice 68 is not placed in an opposing manner with respect to air flow but is placed parallel thereto as orifice 72 will provide the necessary pressure drop and consequently permit sampling air to enter into orifice 67 of sampling tube 73 and across sensing means 70 and out through tubular section 74.

An actual test was conducted utilizing a sensing device of the type shown in FIGS. 1 and 2 except that the sensing means 20 utilized a small air sampling pump as a means of introducing air to the sensing means. However, the test did indicate the practicality of observing the change of humidity (dew point) with time throughout the course of drying. A hose was steamed and rinsed with hot water prior to drying with the drying taking place in approximately 3.5 minutes corresponding to the inflection point of the dew point/time curve. The dew point at this time was 60° F. It subsequently dropped to 10° F. in a total of 5 minutes.

When the hose was rinsed with 12° C. cold water, the drying was predictably slower. Instead of a period of constant humidity at the beginning, the dew point decreased from the start because of the reduced volatility of the water at lower temperature. Nevertheless, this initial period of decreasing dew point was followed by a much more rapid reduction of dew point, signaling the end of the constant drying rate period which is characteristic of surface drying. The point of inflection of the dew point-time curve occurred at about 4.5 minutes with a dew point of 36° F. The final dew point of 10° F. was reached in 10 minutes.

As indicated earlier, the humidity sensor 20 can be interconnected to a signal processor such as 22 which when utilized in conjunction with a drying oven or in conjunction with the drying of a hose, can signal the turning off of either the drying oven or the source of compressed air so as to avoid insufficient drying or overdrying with waste of time and consumption of expensive compressed air or energy. Other advantages utilizing the signal processor in conjunction with the humidity sensor have been previously indicated such as the triggering of an alarm for signaling the end of drying wherein the device is utilized to monitor a drying oven by sampling both the inlet and outlet air.

It will thus be seen that through the present invention there is now provided a simplified sampling unit which can effect the diverting of a sample portion from a mainstream of flowing fluid without a pump or other pressure reduction mechanisms which utilize moving parts. The sensing device of this invention is simple in its fabrication yet can be utilized in a fluid flow stream without requiring filters and their consequent adverse effect on pressure drop. The sensing device can be readily adapted to any piping system and yet avoids the introduction of large particles of moisture or dirt into the sensing means.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A device for diverting and sensing moisture in a sample portion from a main conduit stream of fluid flowing from an upstream to a downstream direction comprising:
    a first conduit member;
    a second conduit member, both said conduit members adapted for fluid-tight communication with said channel and each having an orifice at one end and in open communication with said main conduit, said orifice of said second conduit member being of a larger dimension than said orifice of said first conduit member, said orifices being spaced from each other in said stream with said first orifice being positioned upstream of said second orifice; and
    moisture sensing means adapted for fluid communication with the ends of said conduit members opposite said orifices, said orifices of said first and second conduits adapted to be placed in said stream of fluid with both said orifices facing in a downstream direction with respect to said flow;
    said first and second conduit members and said sensing means defining an open fluid flow path with said conduit stream to thereby effect the flow of fluid from said stream of fluid into said orifice of said first conduit member and in a direction opposite said fluid flow, through said first conduit member, said moisture sensing means, said second conduit member, out of said orifice of said second conduit member and into said stream of fluid.

2. The device for diverting and sensing a sample portion from a main conduit stream as defined in claim 1 wherein said second conduit member and said second orifice are defined by a tubular section having an enlarged diameter section of greater cross sectional dimension than said first conduit member.

3. The device for diverting and sensing a sample portion from a main conduit stream as defined in claim 2 wherein said second conduit member and said second orifice are defined by two tubular sections with said tubular section defining said second orifice having a diameter of greater cross sectional dimension than said first conduit member.

4. The device for diverting and sensing a sample portion from a main conduit stream as defined in claim 1 wherein said moisture sensing means is operatively associated with a signal processor means.

5. The device for diverting and sensing a sample portion from a main conduit stream as defined in claim 1 wherein said moisture sensing means comprises a humidity sensor.

6. The device for diverting and sensing a sample portion from a main conduit stream as defined in claim 1 wherein said main conduit comprises a section of pipe.

7. The device for diverting and sensing a sample portion from a main conduit stream of fluid as defined in claim 1 wherein said stream is comprised of air and water vapor.

* * * * *